US008591399B2

(12) United States Patent
Marescaux et al.

(10) Patent No.: US 8,591,399 B2
(45) Date of Patent: Nov. 26, 2013

(54) SURGICAL METHOD UTILIZING TRANSLUMINAL ENDOSCOPE AND INSTRUMENTS

(75) Inventors: Jacques Francois Bernard Marescaux, Scharrachbergheim (FR); Jeffrey S. Melanson, Sturbridge, MA (US); Bernard Dallemagne, Beauafys (BE); Joel Leroy, Schiltigheim (FR); Didier Raoul Daniel Mutter, Vendenheim (FR); James P. Barry, Charlton, MA (US); Stefan Storz, Wurmlingen (DE); Martin Leonhard, Emmingen (DE)

(73) Assignee: Karl Storz Endovision, Inc., Charlton, MA (US)

( * ) Notice: Subject to any disclaimer, the term of this patent is extended or adjusted under 35 U.S.C. 154(b) by 1476 days.

(21) Appl. No.: 11/863,930

(22) Filed: Sep. 28, 2007

(65) Prior Publication Data

US 2008/0269557 A1    Oct. 30, 2008

Related U.S. Application Data

(63) Continuation-in-part of application No. 11/739,833, filed on Apr. 25, 2007.

(51) Int. Cl.
    *A61B 1/00*          (2006.01)
(52) U.S. Cl.
    USPC ............ 600/106; 600/107; 600/114; 600/115
(58) Field of Classification Search
    USPC .................................. 600/106–107, 114–115
    See application file for complete search history.

(56) References Cited

U.S. PATENT DOCUMENTS

| 3,667,474 A | 6/1972 | Lapkin et al. | |
| 3,896,793 A | 7/1975 | Mitsui et al. | 128/6 |
| 3,915,157 A | 10/1975 | Mitsui | 128/6 |
| 3,924,608 A | 12/1975 | Mitsui | 128/2 |
| 4,436,087 A | 3/1984 | Ouchi | 128/6 |
| 4,653,476 A | 3/1987 | Bonnet | 128/4 |
| 4,949,706 A | 8/1990 | Thon | 128/4 |
| 5,025,778 A | 6/1991 | Silverstein et al. | 128/4 |
| 5,037,433 A | 8/1991 | Wilk et al. | 606/139 |

(Continued)

FOREIGN PATENT DOCUMENTS

| WO | 2005044095 A1 | 5/2005 |
| WO | 2006046263 A1 | 5/2006 |

(Continued)

OTHER PUBLICATIONS

European Search Report & Written Opinion; EP 08 00 7936; Sep. 3, 2009; 7 pages.

*Primary Examiner* — Matthew J Kasztejna
(74) *Attorney, Agent, or Firm* — St. Onge Steward Johnston & Reens LLC

(57) ABSTRACT

A method of transluminal surgery is provided, which utilizes an endoscopic surgery apparatus having pivotable arms attached by hinges on its distal end. The arms are interchangeable with arms of various configurations. The method includes the steps of inserting an endoscopic surgery apparatus into a body cavity of a patient, making an incision in the body cavity wall to allow access to the patient's abdominal cavity, and further inserting the apparatus through the incision. Surgery is performed at the desired surgical site and the apparatus is withdrawn into the body cavity where the incision is closed. Finally, the apparatus is withdrawn from the patient's body.

22 Claims, 8 Drawing Sheets

(56) References Cited

U.S. PATENT DOCUMENTS

| | | | |
|---|---|---|---|
| 5,259,366 A | 11/1993 | Reydel et al. ............... 128/4 |
| 5,312,391 A | 5/1994 | Wilk | |
| 5,353,784 A | 10/1994 | Nady-Mohamed | |
| 5,386,818 A | 2/1995 | Schneebaum et al. .......... 128/4 |
| 5,474,057 A | 12/1995 | Makower et al. | |
| 5,483,951 A | 1/1996 | Frassica et al. ............ 600/104 |
| 5,503,616 A | 4/1996 | Jones ....................... 600/155 |
| 5,569,164 A | 10/1996 | Lurz ........................ 600/158 |
| 5,624,398 A | 4/1997 | Smith et al. | |
| 5,630,782 A | 5/1997 | Adair ....................... 600/133 |
| 5,674,181 A | 10/1997 | Iida | |
| 5,749,889 A | 5/1998 | Bacich et al. ............... 606/198 |
| 5,820,546 A | 10/1998 | Ouchi ....................... 600/123 |
| 5,827,177 A | 10/1998 | Oneda et al. ................ 600/121 |
| 5,833,656 A | 11/1998 | Smith et al. | |
| 5,885,207 A | 3/1999 | Iwasaka .................... 600/139 |
| 5,921,915 A | 7/1999 | Aznoian et al. ............. 600/104 |
| 5,954,692 A | 9/1999 | Smith et al. | |
| 5,993,461 A | 11/1999 | Abae | |
| 5,995,875 A | 11/1999 | Blewett et al. .............. 607/98 |
| 6,059,719 A | 5/2000 | Yamamoto et al. | |
| 6,066,090 A | 5/2000 | Yoon ........................ 600/113 |
| 6,071,233 A | 6/2000 | Ishikawa et al. ............. 600/104 |
| 6,106,521 A | 8/2000 | Blewett et al. ............... 606/41 |
| 6,179,776 B1 | 1/2001 | Adams et al. ............... 600/121 |
| 6,296,635 B1 | 10/2001 | Smith et al. | |
| 6,352,503 B1 | 3/2002 | Matsui et al. ............... 600/104 |
| 6,409,727 B1 | 6/2002 | Bales et al. .................. 606/47 |
| 7,029,435 B2 | 4/2006 | Nakao ....................... 600/153 |
| 7,060,024 B2 | 6/2006 | Long et al. ................. 600/106 |
| 2005/0113640 A1 | 5/2005 | Saadat et al. | |
| 2005/0234294 A1* | 10/2005 | Saadat et al. ............... 600/104 |
| 2005/0234297 A1 | 10/2005 | Devierre et al. | |
| 2006/0189845 A1* | 8/2006 | Maahs et al. ............... 600/146 |
| 2007/0167679 A1 | 7/2007 | Miyamoto et al. ............ 600/106 |
| 2007/0167680 A1 | 7/2007 | Miyamoto et al. ............ 600/106 |
| 2007/0260273 A1 | 11/2007 | Cropper et al. | |
| 2010/0036198 A1* | 2/2010 | Tacchino et al. ............. 600/106 |

FOREIGN PATENT DOCUMENTS

| | | |
|---|---|---|
| WO | 2006110275 A2 | 10/2006 |
| WO | WO 2007/080974 | 7/2007 |
| WO | 2007104397 A1 | 9/2007 |

* cited by examiner

SURGICAL METHOD UTILIZING TRANSLUMINAL ENDOSCOPE AND INSTRUMENTS

CROSS REFERENCE TO RELATED APPLICATIONS

This application is a continuation-in-part of U.S. patent application Ser. No. 11/739,833, entitled "Endoscope System With Pivotable Arms" filed on Apr. 25, 2007. The entire disclosure of U.S. patent application Ser. No. 11/739,833 is hereby incorporated by reference.

FIELD OF THE INVENTION

The present invention relates to a surgical method. More particularly, the present invention relates to a method of transluminal surgery.

BACKGROUND OF THE INVENTION

The traditional method of abdominal surgery involves creating an incision in a patient large enough so that the surgeon can work with and handle directly the patient's organs and tissues. Unfortunately, this traditional method carries with it a relatively high risk of infection due to the exceptional amount of exposure to which the patient's internal organs are subjected during the surgery. Other significant drawbacks associated with traditional methods of abdominal surgery are the length of recovery time required for a patient and the significant pain suffered because of the size of the incision.

These negative effects of surgical treatment were significantly mitigated by the introduction of endoscopic surgery. Endoscopic surgery generally involves making one or more relatively small incisions in a patient's abdomen and then inserting one or more small surgical tools. The surgical tools are generally mounted on one end of a long, thin element having on the other end a handle and a means for actuating or manipulating the surgical tool. The endoscopic surgical tools are also often outfitted with optical and light-delivery channels so that the surgeon can view the area of the surgery.

While the advent of endoscopic surgical techniques significantly reduced the drawbacks of traditional surgical techniques, endoscopic surgery still involves a relatively high risk of infection, a relatively long recovery period, and significant pain for the patient. Recently, these negative effects have been even further reduced by the introduction of transluminal endoscopic surgery.

In transgastric surgery, which is a type of transluminal surgery which utilizes a patient's gastric tract, an endoscopic tool is inserted into the patient's mouth and fed to the patient's stomach. The wall of the patient's stomach can then be punctured so that the tool can access other parts of the patient's abdomen. An incision in the wall of the stomach is preferable to external incisions because there are no nerve endings in the stomach. Transluminal endoscopic surgery reduces patient pain and recovery time as well as the risk of infection. In other types of transluminal surgery, the endoscopic tool is inserted into a patient's rectum, colon, or vagina. All or nearly all locations in a patient's abdominal cavity can be accessed via at least one of these body cavities.

Methods of transluminal surgery traditionally require the use of a complicated endoscopic tool. The endoscopic tool that is inserted into the patient for transluminal surgery generally includes one or more surgical tools, an optical channel, one or more light channels, and/or one or more channels for evacuation or insufflation. The tools often have other unique features. First, they preferably are designed such that insertion into the patient's body is easy and causes the patient a minimum of trauma. Second, the tool preferably provides a means for multiple surgical tools to be used to exert force or perform functions in multiple directions at the surgical site. This is more difficult in transluminal surgery because there is only one possible angle of approach since the tools are preferably inserted in the same place, for example, the patient's mouth. In conventional endoscopic surgery on the other hand, tools can be inserted at multiple locations so that the surgeon has an advantageous 'working triangle.' The working triangle allows the surgeon to exert force in multiple directions and therefore better perform surgical tasks. In transluminal surgery it is more difficult to create this working triangle since the tools are inserted parallel to one another.

There are various examples in the prior art of endoscopic tools which are intended for or could be used in transluminal surgery and which attempt to address the concerns described above. For example, U.S. Pat. No. 6,066,090 to Yoon, U.S. Pat. No. 6,352,503 to Matsui et al., and U.S. Pat. No. 7,029,435 to Nakao all disclose endoscopic surgical apparatuses which can be used in transluminal surgical techniques.

A significant drawback which all of these endoscopic surgical systems have in common is that they are complicated to deploy. This disadvantage is particularly important in methods of transluminal surgery because the system must be capable of quickly and easily switching between a state in which the system is easily moved through a patient's body cavities and a state in which the surgical tools are 'triangulated.' During a typical transluminal procedure, the system may be switched between these two states at least three times. The capabilities of the endoscopic tool or tools employed by the surgeon are vital to the ease, efficiency, and ultimately the success of any transluminal surgical procedure.

Therefore, what is needed is a method for performing transluminal surgery which minimizes the strain on a surgical patient, minimizes the patient's recovery time, reduces the risk to the patient of infection, and is effective for a wide variety of surgical procedures.

SUMMARY OF THE INVENTION

It is an object of the present invention to provide a method for transluminal surgery which minimizes the strain on a surgical patient.

It is a further object of the present invention to provide a method for transluminal surgery which minimizes the patient's recovery time.

It is yet a further object of the present invention to provide a method for transluminal surgery which reduces the risk to the patient of infection.

It is still a further object of the present invention to provide a method for transluminal surgery which is effective for a wide variety of surgical procedures.

These and other objects are accomplished by one embodiment of the present invention which provides a method of transluminal surgery, comprising the steps of: first providing an endoscopic surgery apparatus including a tubular member having a plurality of channels along its longitudinal axis, a handle located on a proximal end of the tubular member, two or more arms pivotably connected to a distal end of the tubular member by hinges, wherein the arms have guiding channels passing therethrough adapted to receive endoscopic surgical tools. Then, inserting the distal end of the tubular member through a natural body orifice into a body cavity with the arms in a closed position; creating an incision in the body cavity wall sized to accommodate the tubular member using at least one endoscopic surgical tool; advancing the distal end of the tubular member through the incision to a desired surgical site; pivoting the arms about the hinges into an open position using a mechanism on the handle such that the guiding channels passing through the arms create a desired degree of triangulation for endoscopic surgical tools disposed in the guiding channels; performing at least one surgical task at the surgical site; pivoting the arms about the hinges into a closed position using a mechanism on the handle.

In some embodiments, the step of creating an incision in a body cavity wall further comprises the steps of pivoting the arms about the hinges into an open position using a mechanism on the handle such that the guiding channels passing through the arms create a desired degree of triangulation for endoscopic surgical tools disposed in the guiding channels; using at least one endoscopic surgical tool to create the incision; and pivoting the arms about the hinges into a closed position using a mechanism on the handle.

In some embodiments, the step of creating an incision in a body cavity wall further comprises the steps of advancing an endoscopic surgical tool from the tubular member through an opening between the arms, wherein the arms include a ramp for deflecting the endoscopic surgical tool; using the endoscopic surgical tool to create the incision; and withdrawing the endoscopic surgical tool into the tubular member.

In some embodiments, the step of providing an endoscopic surgery apparatus further comprises that the arms are interchangeable with arms of different configurations and also includes the step of selecting two arms having a desired configuration from a group of interchangeable arms of different configurations. In some embodiments, the step of providing an endoscopic surgery apparatus further comprises that one of the channels is an optical channel for the transmission of images and at least one other of the channels is an illumination channel for the transmission of light and when the arms are in the closed position an opening is defined for viewing of an area proximal to the distal end via the optical channel and illumination of an area proximal to the distal end via the at least one illumination channel; and the step of advancing the distal end of the tubular member to a desired surgical site further comprises the step of using the optical channel to view an area proximal to the distal end of the tubular member.

According to a second embodiment of the present invention, a method of transluminal surgery is provided, comprising the steps of first providing an endoscopic surgery apparatus including a tubular member having a plurality of channels along its longitudinal axis, a handle located on a proximal end of the tubular member. Then, selecting two arms having a desired configuration from a group of interchangeable arms of different configurations, to be pivotably connected to a distal end of the tubular member by hinges, and the arms have guiding channels passing therethrough adapted to receive endoscopic surgical tools; inserting the distal end of the tubular member through a natural body orifice into a body cavity with the arms in a closed position; creating an incision in the body cavity wall sized to accommodate the tubular member using at least one endoscopic surgical tool; advancing the distal end of the tubular member through the incision and to a desired surgical site; advancing the distal end of the tubular member to a desired surgical site; pivoting the arms about the hinges into an open position using a mechanism on the handle such that the guiding channels passing through the arms create a desired degree of triangulation for endoscopic surgical tools disposed in the guiding channels; performing at least one surgical task at the surgical site; and pivoting the arms about the hinges into a closed position using a mechanism on the handle.

In some embodiments, the step of providing an endoscopic surgery apparatus further comprises that one of the channels is an optical channel for the transmission of images and at least one other of the channels is an illumination channel for the transmission of light and when the arms are in the closed position an opening is defined for viewing of an area proximal to the distal end via the optical channel and illumination of an area proximal to the distal end via the at least one illumination channel; and the step of advancing the distal end of the tubular member to a desired surgical site further comprises the step of using the optical channel to view an area proximal to the distal end of the tubular member. In some embodiments, the step of identifying a location in a body cavity wall further comprises the step of using the optical channel to view the area in front of the distal end of the tubular member.

In some embodiments, the step of creating an incision in a body cavity wall further comprises the steps of pivoting the arms about the hinges into an open position using a mechanism on the handle such that the guiding channels passing through the arms create a desired degree of triangulation for endoscopic surgical tools disposed in the guiding channels; using at least one endoscopic surgical tool to create the incision; and pivoting the arms about the hinges into a closed position using a mechanism on the handle.

In some embodiments, the step of creating an incision in a body cavity wall further comprises the steps of advancing an endoscopic surgical tool from the tubular member through an opening between the arms, wherein the arms include a ramp for deflecting the endoscopic surgical tool; using the endoscopic surgical tool to create the incision; and withdrawing the endoscopic surgical tool into the tubular member.

According to a third embodiment of the present invention, a method of transluminal surgery is provided, comprising the steps of first providing an endoscopic surgery apparatus including a tubular member having a plurality of channels along its longitudinal axis, a handle located on a proximal end of the tubular member, two or more arms pivotably connected to a distal end of the tubular member by hinges and having guiding channels passing therethrough adapted to receive endoscopic surgical tools, wherein at least one of the channels of the tubular member is an optical channel for the transmission of images and at least one other of the channels is an illumination channel for the transmission of light, and wherein when the arms are in the closed position an opening is defined allowing for viewing of an area proximal to the distal end via the optical channel and illumination of the area proximal to the distal end via the at least one illumination channel. Then, inserting the distal end of the tubular member through a natural body orifice with the arms in a closed position; advancing the distal end of the tubular member into a body cavity using the optical channel to view the body cavity; creating an incision in the body cavity wall sized to accommodate the tubular member using at least one endoscopic surgical tool; advancing the distal end of the tubular member through the incision into the abdominal cavity; advancing the distal end of the tubular member to a desired surgical site using the optical channel to view the abdominal cavity; pivoting the arms about the hinges into an open position using a mechanism on the handle such that the guiding channels passing through the arms create a desired degree of triangulation for endoscopic surgical tools disposed in the guiding channels; performing at least one surgical task at the surgical site; and pivoting the arms about the hinges into a closed position using a mechanism on the handle.

In some embodiments, the step of creating an incision in a body cavity wall further comprises the steps of pivoting the arms about the hinges into an open position using a mechanism on the handle such that the guiding channels passing through the arms create a desired degree of triangulation for endoscopic surgical tools disposed in the guiding channels; using at least one endoscopic surgical tool to create the incision; and pivoting the arms about the hinges into a closed position using a mechanism on the handle.

In some embodiments, the step of creating an incision in a body cavity wall further comprises the steps of advancing an endoscopic surgical tool from the tubular member through the opening between the arms, wherein the arms include a ramp for deflecting the endoscopic surgical tool; using the endoscopic surgical tool to create the incision; and withdrawing the endoscopic surgical tool into the tubular member.

In some embodiments, the step of providing an endoscopic surgery apparatus further comprises that the arms are interchangeable with arms of different configurations and the method further comprises the step of selecting two arms of a desired configuration from a group of interchangeable arms of different configurations.

In some embodiments, the method further comprises the step of closing the incision in the body cavity wall using at least one endoscopic surgical tool to attach a surgical clip to the incision. In some embodiments, the method further comprises the step of closing the incision in the body cavity wall using at least one endoscopic surgical tool to suture the incision. In some embodiments, the step of closing the incision is performed by a suturing system incorporated into the arms. In some embodiments, the method further comprises the step of closing the incision in the body cavity wall using at least one endoscopic surgical tool to employ an endoloop to the incision.

According to yet another embodiment of the present invention, a method of transluminal surgery is provided, comprising the steps of first providing an endoscopic surgery apparatus including a tubular member having a plurality of channels along its longitudinal axis, a handle located on a proximal end of the tubular member; wherein at least one of the channels of the tubular member is an optical channel for the transmission of images and at least one other of the channels is an illumination channel for the transmission of light. Then, selecting two arms having a desired configuration from a group of interchangeable arms of different configurations, to be pivotably connected to a distal end of the tubular member by hinges, wherein the arms have guiding channels passing therethrough adapted to receive endoscopic surgical tools and wherein when the arms are in a closed position an opening is defined allowing for viewing of an area proximal to the distal end via the optical channel and illumination of the area proximal to the distal end via the at least one illumination channel; inserting the distal end of the tubular member through a natural body orifice into a body cavity with the arms in a closed position; advancing the distal end of the tubular member into a body cavity using the optical channel to view the body cavity; creating an incision in the body cavity wall sized to accommodate the tubular member using at least one endoscopic surgical tool in at least one channel of the tubular member to the body cavity wall; advancing the distal end of the tubular member into the abdominal cavity through the incision; advancing the distal end of the tubular member to a desired surgical site using the optical channel to view the abdominal cavity; pivoting the arms about the hinges into an open position using a mechanism on the handle such that the guiding channels passing through the arms create a desired degree of triangulation for endoscopic surgical tools disposed in the guiding channels; performing at least one surgical task at the surgical site; pivoting the arms about the hinges into a closed position using a mechanism on the handle; withdrawing the distal end of the tubular member via the incision in the body cavity wall into the body cavity; closing the incision in the body cavity wall using at least one endoscopic surgical tool; and withdrawing the distal end of the tubular member from the natural body orifice.

In some embodiments, the step of creating an incision in a body cavity wall further comprises the steps of pivoting the arms about the hinges into an open position using a mechanism on the handle such that the guiding channels passing through the arms create a desired degree of triangulation for endoscopic surgical tools disposed in the guiding channels; using at least one endoscopic surgical tool to create the incision; and pivoting the arms about the hinges into a closed position using a mechanism on the handle.

In some embodiments, the step of creating an incision in a body cavity wall further comprises the steps of advancing an endoscopic surgical tool from the tubular member through the opening between the arms, wherein the arms include a ramp for deflecting the endoscopic surgical tool; using the endoscopic surgical tool to create the incision; and withdrawing the endoscopic surgical tool into the tubular member.

In some embodiments, the step of performing at least one surgical task at the surgical site comprises the step of providing an endoscopic retrieving bag for the removal of dissected tissue. In some embodiments, the step of closing the incision in the body cavity wall using at least one endoscopic surgical tool further comprises the step of attaching a surgical clip to the incision. In some embodiments, the step of closing the incision in the body cavity wall using at least one endoscopic surgical tool further comprises the step of suturing the incision. In some embodiments, the step of suturing the incision is performed by a suturing system incorporated into the arms.

In some embodiments, the step of closing the incision in the body cavity wall using at least one endoscopic surgical tool further comprises the step of employing an endoloop to the incision. In some embodiments, the step of performing at least one surgical task at the surgical site comprises the step of employing a cauterizing endoscopic surgical tool. In some embodiments, the step of performing at least one surgical task at the surgical site comprises the step of employing a laser.

In some embodiments, the step of providing an endoscopic surgery apparatus further comprises that the distal end of the tubular member articulates. In some embodiments, the step of advancing the distal end of the tubular member to a desired surgical site further comprises the step of articulating the distal end of the tubular member into a desired position relative to a surgical site. In some embodiments, the steps of pivoting the arms about the hinges into an open position a first and a second time further comprise the step of displacing tissue using the arms.

In some embodiments, the step of selecting two arms having a desired configuration includes selecting arms adapted to grasp tissue, cut tissue, or displace tissue when the arms are pivoted about their hinges. In some embodiments, the step of selecting two arms having a desired configuration includes selecting arms which form an obturator shape when the arms are in a closed position.

In some embodiments, the step of advancing the distal end of the tubular member to a desired surgical site further comprises the step of pivoting the arms about the hinges into an open position an additional time using a mechanism on the handle so as to provide a wider view of an area proximal to the distal end via an optical channel disposed in the tubular member.

In some embodiments, the step of advancing the distal end of the tubular member to a desired surgical site further comprises the steps of insufflating the abdominal cavity using an insufflation channel disposed in the tubular member and monitoring the pressure in the abdominal cavity in the region adjacent to the distal end of the tubular member via an insufflation channel disposed in the tubular member. In some embodiments, the step of performing at least one surgical task at the surgical site further comprises the step of introducing a device for delivery of fluid or gaseous matter through a channel in the tubular member for the delivery of fluid or gaseous matter to the surgical site. In some embodiments, further comprising the step of using the arms to hold tissue resected from a patient's body for removal from the patient's body.

DETAILED DESCRIPTION OF THE DRAWINGS

Figure 1:
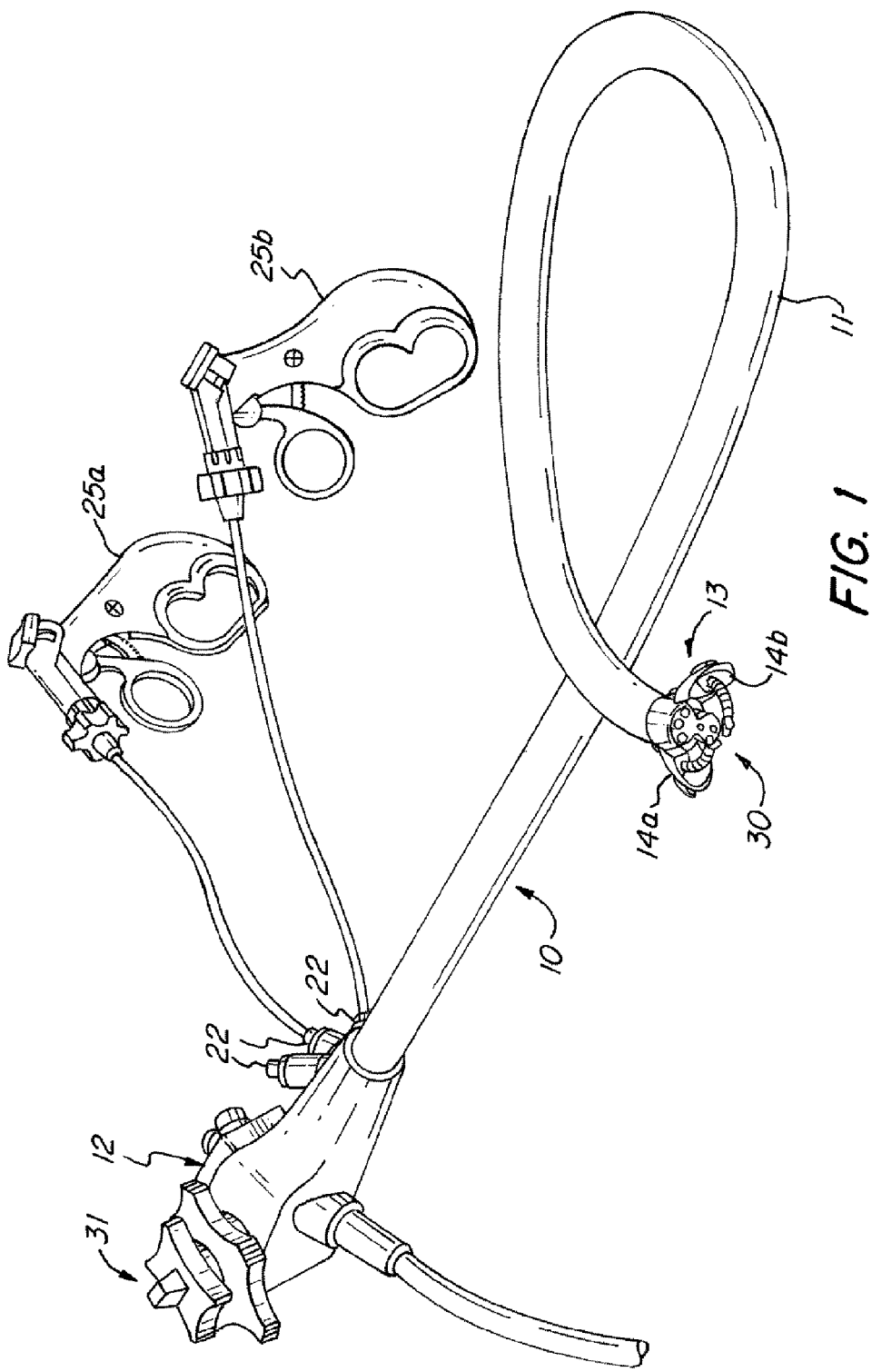
FIG. 1 is a perspective view of an endoscopic surgery apparatus for use in a method according to one embodiment of the present invention.

A method of transluminal surgery according to an embodiment of the present invention utilizes an endoscopic surgery apparatus such as apparatus 10 shown in FIG. 1. The endoscopic surgery apparatus 10 includes tubular member 11 and handle 12 which is located on a proximal end 31 of tubular member 11. At the distal end 30 of tubular member 11 is a head portion 13 of the apparatus 10, having two pivotable arms 14a and 14b fixed thereon. The arms 14a and 14b are attached by hinges to the head portion 13 of the apparatus 10. Two surgical tools 25a and 25b are also shown in FIG. 1. The surgical tools 25a and 25b are shown inserted into the endoscopic surgery apparatus 10 at proximal terminals 22 of working channels running along the longitudinal axis of the tubular member 11. The surgical tools utilized with apparatus 10, such as tools 25a and 25b, generally have tools and articulating portions on their distal ends which are controlled using a handle portion on a proximal end.

The term "tubular member" as used throughout this application refers to many possible configurations. In one embodiment, the tubular member 11 has a shaft at its proximal end that is attached to the handle 12 and is substantially inflexible. Attached to the shaft portion is a series of articulating vertebrae, the articulation of which is controlled by the surgeon using control mechanisms on the handle. In that embodiment, the head portion 13 is either the last vertebra of the series of vertebrae or a special member attached to the last vertebra. In another embodiment, the tubular member 11 could be a single element, constructed out of a flexible material designed to have a selected degree of plasticity and elasticity. In that embodiment, the head portion 13 may or may not be a separate element distinct from the tubular member 11, but merely the most distal portion of the tubular member 11.

Figure 2:
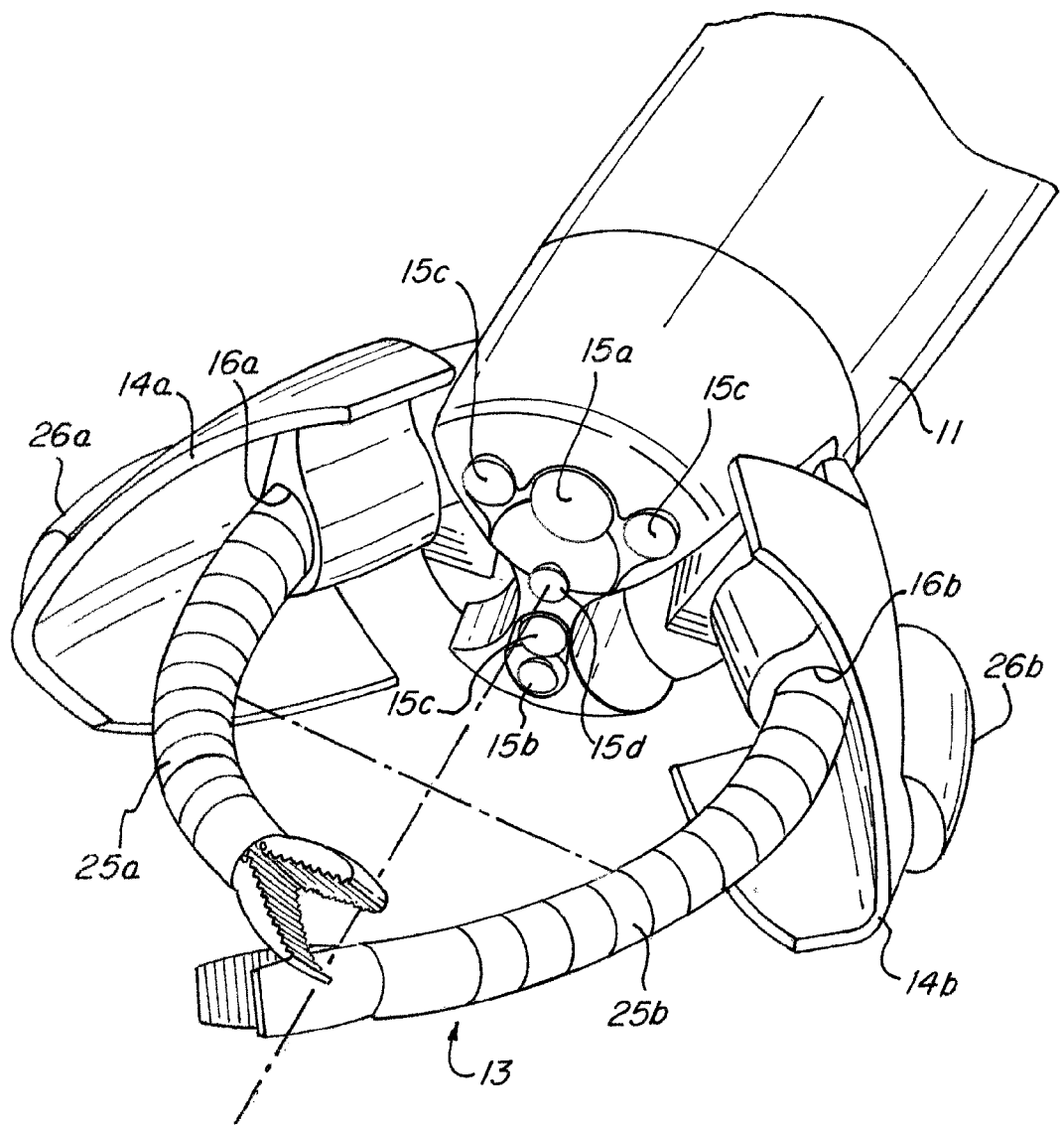
FIG. 2 is a perspective view of the distal end of the endoscopic surgery apparatus of FIG. 1 showing the arms in an open position and surgical tools protruding from the working channels therein.

FIG. 2 shows a close-up view of the head portion 13 of the endoscopic surgery apparatus 10. Arms 14a and 14b are shown in an open position. The arms 14a and 14b include the guiding channels 16a and 16b, which align with working channels passing through tubular member 11 (not visible in FIG. 2). Guiding channels 16a and 16b receive and guide surgical tools 25a and 25b which are shown protruding from the guiding channels 16a and 16b. The angle of arms 14a and 14b determines the angle that surgical tools 25a and 25b approach a surgical site. The surgeon may select an angle for the arms 14a and 14b such that the surgical tools 25a and 25b emerge parallel to each other, at an angle less than parallel, or at an angle more than parallel. The configuration of arms 14a and 14b will affect the degree to which the arms can be opened. In the embodiment shown in FIG. 2, arms 14a and 14b have tissue displacing members 26a and 26b formed on their outer surface for manipulating and displacing tissue. In many embodiments, arms 14a and 14b do not include displacing members 26a and 26b but such arms are still advantageously used to temporarily displace and manipulate tissue. Further, in some embodiments the head portion 13 of an endoscopic surgery apparatus 10, including the arms 14a and 14b, is electrically isolated so as to enable electrosurgical procedures.

FIG. 2 also shows the distal terminals of channels 15a-d, wherein channel 15a is an optical channel, channel 15b is a third working channel, channels labeled 15c are illumination channels, and channel 15d is a fluid or air channel. In general, illumination channels 15c provide light to the surgical site so that the surgeon may view the site via the optical channel 15a. Fluid or air channel 15d may be used to deliver air, water, pharmaceutical fluids, or the like to the surgical site. Fluid or air channel 15d is used in some embodiments to provide insufflation in the vicinity of the distal end 30 of the apparatus 10. In some embodiments, working channel 15b is used for insufflation. Fluid or air channel 15d may also be used as a means for sensing the ambient pressure at the surgical site. Alternatively, pressure-sensing may be accomplished at other points on the head portion 13. The third working channel 15b may be advantageously employed as a means for evacuating fluids from the surgical site. In some embodiments, small particles of solid matter may also be evacuated by channel 15b.

The third working channel 15b does not pass through the guiding channels 16a and 16b in arms 14a and 14b. This gives the surgeon the ability to easily exert force in directions parallel to the axis of the tubular member 11. Thus, the surgeon is provided with the ability to exert force in many directions at the surgical site: forward or backward along the axis of the tubular member 11 or at various angles according to the angles of arms 14a and 14b.

Figure 3:
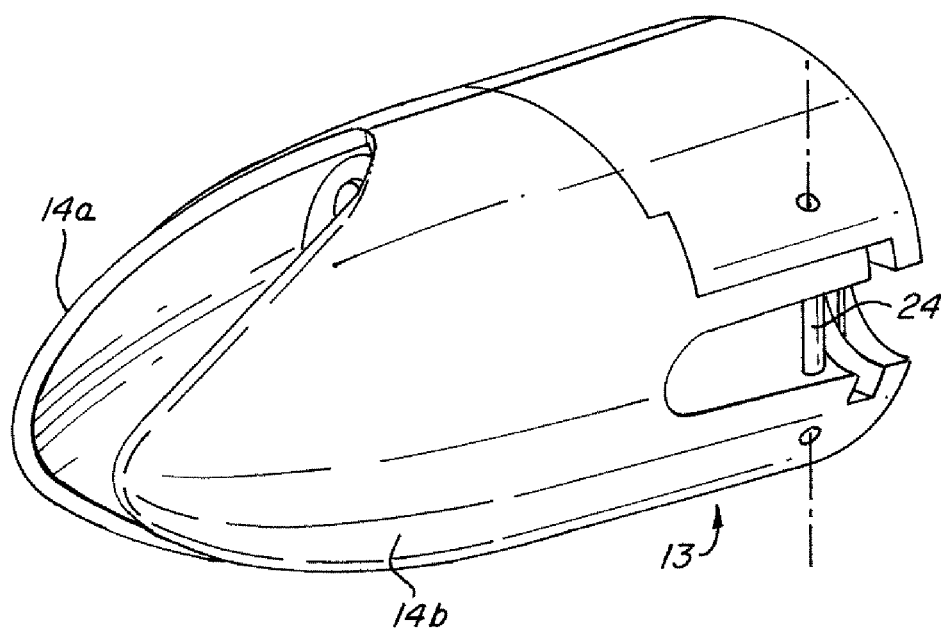
FIG. 3 is a perspective view of the distal end of the endoscopic surgery apparatus of FIG. 1, with arms in a closed position.

FIG. 3 shows head portion 13 of the endoscopic surgery apparatus 10 with arms 14a and 14b in a closed position. A hinge 24 is shown, which pivotably connects the arm 14b to the head portion 13. Arm 14a is connected to tubular member 11 in the same fashion, however this connection is not shown in FIG. 3. In the closed position, arms 14a and 14b provide a ramp for a surgical tool or instrument passing through working channel 15b in some embodiments. This ramp is formed by the shape of the arms 14a and 14b or by protruding members formed on the inner surface of the arms 14a and 14b. This ramp brings the tool or instrument directly into the field of view of optical channel 15a.

Figure 4:
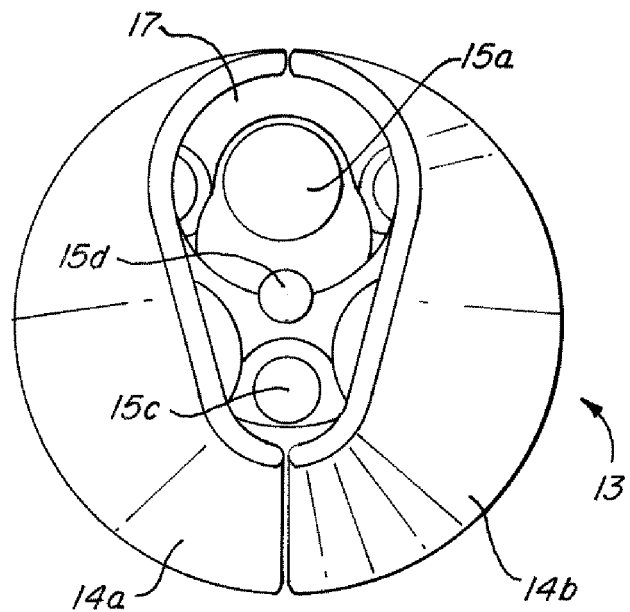
FIG. 4 is an end view of the distal end of the endoscopic surgery apparatus of FIG. 1, with arms in a closed position.

FIG. 4 shows an alternative view of the head portion 13 of the endoscopic surgery apparatus 10 with arms 14a and 14b in a closed position. This view shows one advantageous configuration of the apparatus 10, in which when the arms 14a and 14b are in a closed position, they define an opening 17. The opening 17 allows for utilization of the optical channel 15a, the fluid delivery channel 15d, and at least one of the illumination channels 15c in this embodiment even when the arms 14a and 14b are in a closed position. This allows a surgeon to more safely and effectively employ the endoscopic surgery apparatus 10, for example, during insertion of the apparatus into the body of a patient. Also, as stated above, the arms 14a and 14b provide a ramp for a surgical tool emerging from working channel 15b.

Methods according to the present invention require the performance of a variety of surgical tasks. In order to maximize the efficiency of these methods, the surgical apparatus 10 is advantageously employed in methods according to the present invention using arms of various configurations. The various configurations of arms are interchangeable in the endoscopic surgery apparatus and one set of arms can be easily substituted for another set. Because of the wide variety of surgical procedures which employ the method according to the present invention, arms having different configurations are desirable for optimal performance of the system. The optimal arm configuration depends, for example, on such things as the organ on which surgery is to be performed, the type of surgery to be performed, or the condition of the patient.

For example, in some embodiments the arms 14a and 14b are constructed out of transparent material so that the optical channel 15a and the illumination channels 15c may be utilized even when the arms are in a closed position. In such a design, the opening 17 shown in FIG. 4 may not be necessary and the arms 14a and 14b could completely cover the head portion 13 of the endoscopic surgery apparatus 10. This configuration further eases insertion of the system into a patient. As a second example, in some embodiments the outer surface of the arms provides a means for tissue manipulation at the surgical site. The outer surface could have members formed thereon for displacing tissue. In such a case, the arms are used to move tissue aside or obtain the desired degree of stretching of tissue. In a further example, the arms may also grasp tissue or organs to stabilize or remove them from the surgical site. Finally, some arm configurations may include a blade for snipping or cutting tissue. Certain arm configurations will perform these tasks better than other configurations. Thus, it is highly desirable to have the ability to interchange the arms located on the head portion 13 or even the entire head portion itself.

Most arm configurations that are advantageously employed in the present invention have a shape such that when the arms are in a closed position, they act as an obturator or blunt-tip trocar. This obturator or blunt-tip trocar shape allows for easier insertion into the body because arms of this shape will harmlessly and temporarily displace tissue during insertion.

Figure 5:
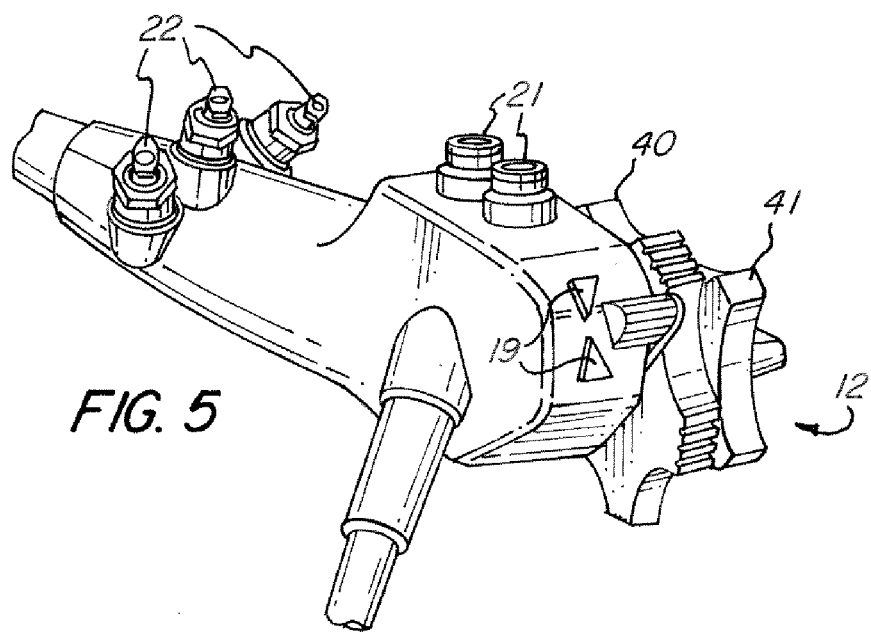
FIG. 5 is a perspective view of the handle on the proximal end of the endoscopic surgery apparatus of FIG. 1.
Figure 6:
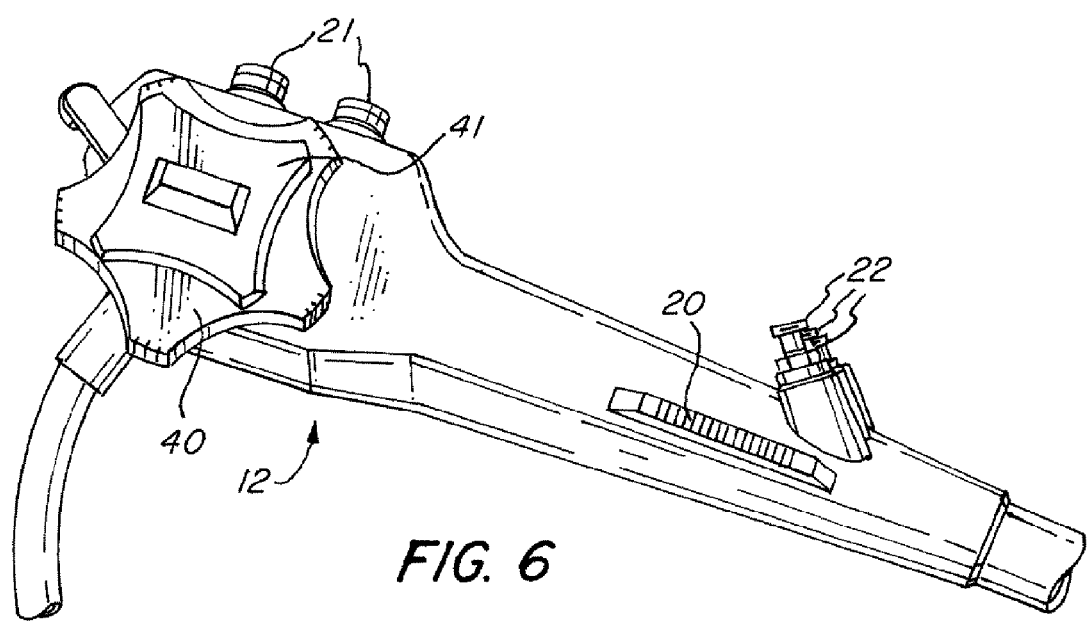
FIG. 6 is a second perspective view of the handle on the proximal end of the endoscopic surgery apparatus of FIG. 1.

FIGS. 5 and 6 show a close-up view of the handle 12 according to one embodiment of the invention. The handle 12 is attached at a proximal end of tubular member 11. The proximal terminals 22 of working channels 16a, 15b, and 16b as well as the proximal terminals 21 of the fluid or air channel 15d are shown. Camera controls 19 for controlling optical components utilizing the optical channel 15a are shown in FIG. 5. In some embodiments, the camera controls 19 control the degree of focus and zoom of the camera so that the surgeon is ensured a clear view of the surgical site. In some embodiments of the present invention, the system is advantageously adapted to permit video recording of the surgery for later analysis or educational purposes. FIGS. 5 and 6 also show dial controls 40 and 41 which control the articulation and positioning of the distal end of the apparatus 10.

FIG. 6 also shows control switch 20 for controlling the position of the arms on the distal end. The control switch 20 may be of the sliding type as shown, a rotatable knob type, or any other appropriate design. In some embodiments, this switch advantageously has a locking mechanism so that the arms can be locked in a position selected by the surgeon.

Figure 7:
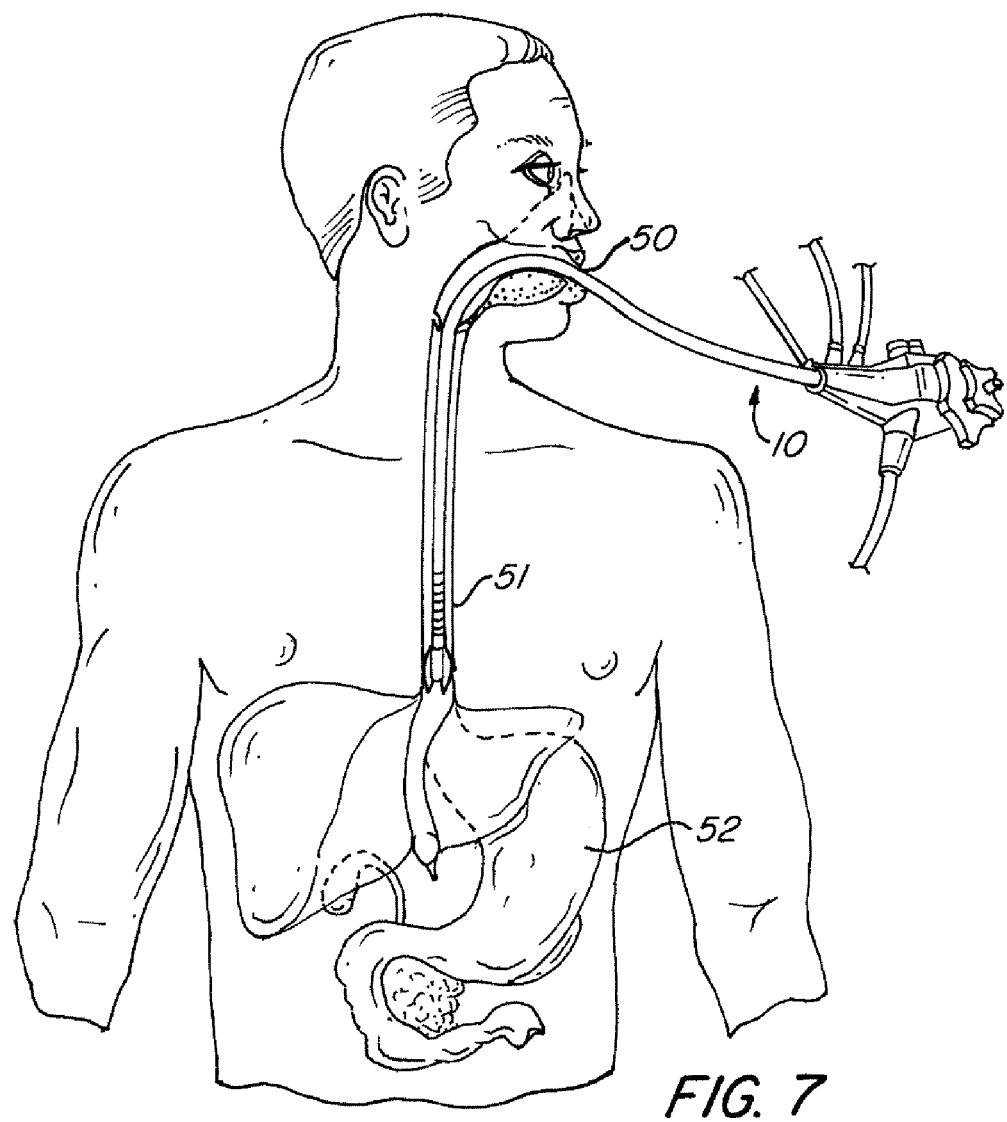
FIG. 7 is a schematic view of the endoscopic surgery apparatus of FIG. 1 being inserted into the esophagus of a patient as a step in a method according to one embodiment of the present invention.
Figure 8:
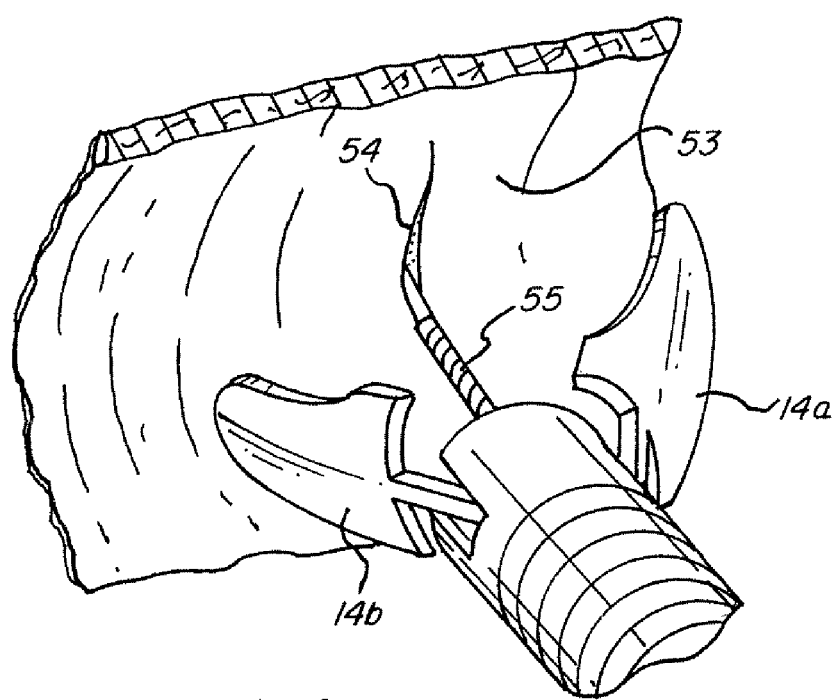
FIG. 8 is a schematic view of the distal end of the endoscopic surgery apparatus of FIG. 1 in the stomach of a patient.
Figure 9:
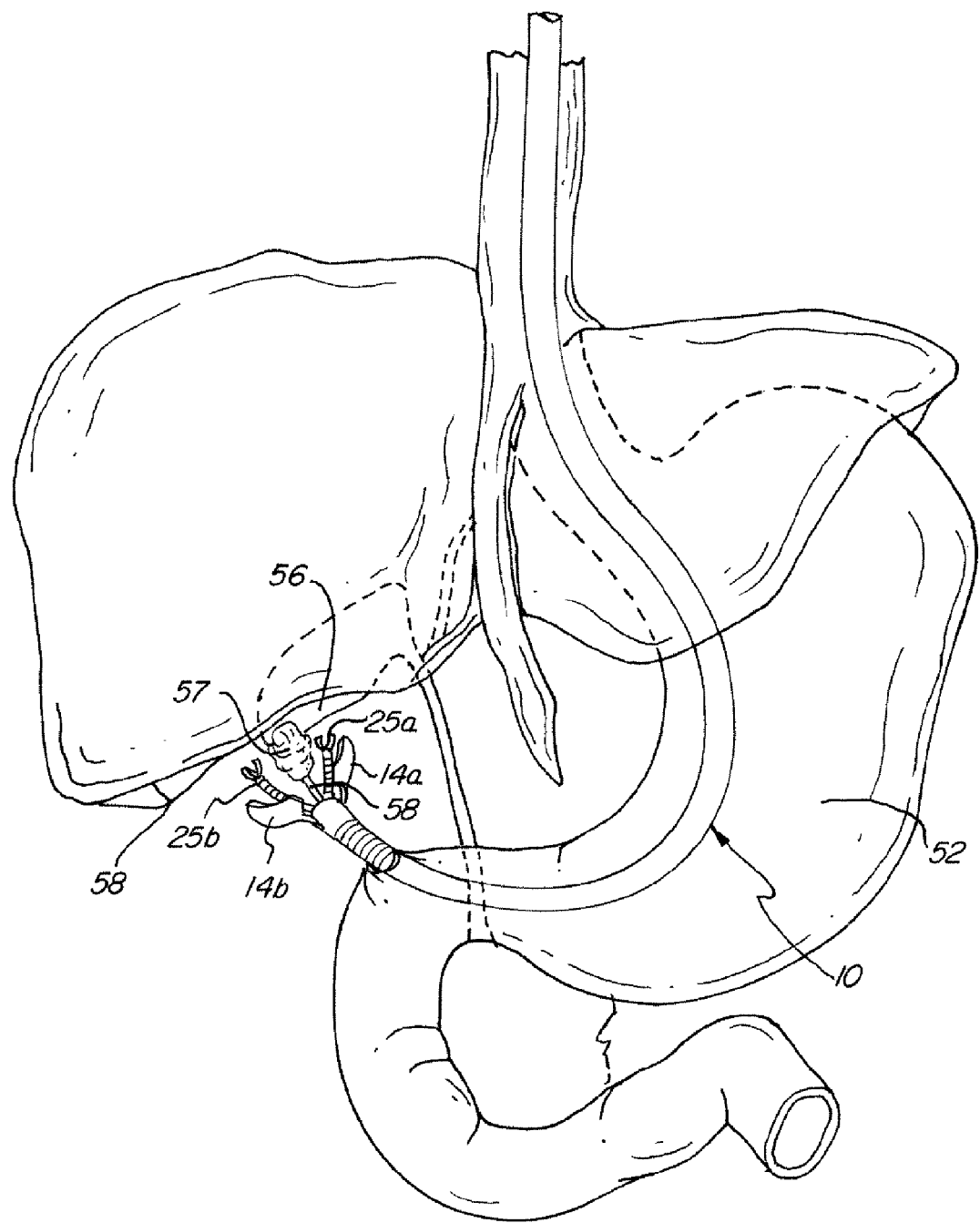
FIG. 9 is a schematic view of the endoscopic surgery apparatus of FIG. 1 performing a gallbladder dissection as part of a method according to one embodiment of the present invention.

The following is an exemplary method of gallbladder dissection according to the present invention which utilizes an endoscopic surgery apparatus such as that just described. FIGS. 7-9 show illustrations at key points in the method. First, an endoscopic surgery apparatus is provided and appropriate pivotable arms are selected. The configuration of the arms will depend on the particular surgery, and could include arms adapted to grasp, cut, and/or displace tissue. Then, as shown in FIG. 7, the endoscopic surgery apparatus 10 is inserted into a patient's mouth 50 and advanced down the patient's esophagus 51. During this step, the arms are in a closed position to minimize strain and trauma on the patient. The endoscopic surgery apparatus is advanced into the stomach 52. The apparatus is guided during insertion with a high degree of accuracy even when the arms are in the closed position using the optical and illumination channels. This is possible either because of the advantageous opening 17 present between the pivotable arms 14 or because the arms 14 are constructed out of a transparent material.

Once the distal end of the apparatus 10 reaches the stomach, the anterior gastric wall 53 is identified. It is intended that the apparatus 10 will be moved through an incision made at the appropriate location in this part of the stomach. To make the necessary incision 54, the arms 14a and 14b of the apparatus 10 are pivoted about their hinges into an open position and a deflectable hook or cutting needle 55 is advanced through one of the working channels of the apparatus 10. The hook or cutting needle 55 is then used to create a gastrotomy 54 sized to accommodate the endoscopic surgery apparatus 10. Once this is done, the arms 14a and 14b are pivoted about their hinges to a closed position, creating the obturator or blunt-tip trocar shape, and the distal end of the apparatus is advanced through the gastrotomy and into the peritoneal cavity.

In some embodiments, the incision 54 is created by advancing a tool 55 in the working channel 15b and making the incision 54 with the arms 14a and 14b in a closed position. The tool 55 will, in some embodiments, be deflected by a ramp formed by the arms 14a and 14b when they are in a closed position. The tool 55 will be brought into the surgeon's field of view and the proper incision 54 may be made.

Once inside the peritoneal cavity, the arms are pivoted about their hinges into an open position if a wide view via the optical channel is desired. The distal end is then articulated in a 'retroflex' maneuver in order to access the right upper abdominal quadrant and to identify the gallbladder 56. During this process, insufflation is often desired and is accomplished using a channel of the endoscopic surgery apparatus (such as the fluid delivery channel 15d). The intra-peritoneal pressure is also monitored using a channel of the endoscopic surgery apparatus. In some embodiments, the pivoting of the arms also serves to displace tissue to a selected degree to achieve a desired amount of stretching or to create more room for the performance of surgical tasks.

The gallbladder 56 is then manipulated using surgical tools 25a and 25b introduced through the working channels and the guiding channels 16a and 16b of the arms. A third surgical tool 58, such as an irrigation-aspiration device, may be introduced through the third working channel 15b. Triangulation of the surgical tools is achieved as a result of the angle of the arms in their open position.

The gallbladder 56 and its pedicle are dissected using a blunt coagulation tip on one of the surgical tools. The cystic duct is isolated, clipped, and divided with articulated scissors. After completing the dissection of the gallbladder from the liver, the gallbladder is placed in an endoscopic retrieving bag 57 which was advanced to the surgical site parallel to the endoscopic surgery apparatus 10. In some embodiments, the endoscopic retrieving bag 57 is advanced down the working channel 15b and then expanded as it exits the apparatus 10. Once the gallbladder is in the bag 57, in such embodiment, it may be held between and within the arms 14a and 14b in a closed position while the apparatus 10 is withdrawn from the patient. Many other surgical tasks are possible using surgical tools introduced through the working channels. Such surgical tools include cauterizing tools, lasers, clippers, cutters, and the like.

The surgical tools are withdrawn from the surgical site and back through the guiding channels 16a and 16b so that the arms may be pivoted into a closed position. The apparatus 10 and the retrieving bag 57 are withdrawn from the peritoneal cavity into the stomach. Once the apparatus 10 is again in the stomach 52, the arms are pivoted to an open position which again creates triangulation of the surgical tools which are necessary to close the gastrotomy 54. The gastrotomy 54 is closed by such means as surgical clips, suture, endoloop, or the like. In some embodiments, the configuration of the arms includes a suturing system incorporated into the arms themselves.

In order to remove the retrieving bag containing the gallbladder through the patient's mouth, the apparatus 10 must first be completely removed. After closing the gastrotomy 54, the arms of the apparatus 10 are pivoted into a closed position and the apparatus 10 is completely withdrawn from the body of the patient. Finally, the retrieving bag 57 is withdrawn via the patient's mouth.

In addition to gallbladder dissection procedures such as that just described, the methods of the present invention are applied to a wide variety of other surgical procedures. These procedures include, but are not limited to, appendectomy, splenectomy, mucosectomy, cholecystectomy, liver resection, small bowel enteroscopy, small bowel resection, tubal ligation, gastrointestinal fistulas, peritoneoscopy, fundoplication, gastroplasty, gastro-entero-anastomosis, adrenalectomy, common bile duct exploration, ileo-cecal resection, ileoplasty, and endoluminoplasty.

Some embodiments of the method according to the present invention are performed under robotic or electronic control. This allows for highly precise and effective remote surgery.

The simplicity of the method of the present invention is well illustrated by an analogy to traditional laparoscopic methods. In a traditional laparoscopic method, a trocar having a tip and sheathed in a cannula is inserted into the patient's abdomen. In order to proceed with the surgery, the tip must be removed so that surgical tools will have access to the surgical site. The method of the present invention is much simpler, as the blunt-tip trocar shaped arms are quickly and easily pivoted into and out of position. Thus, it is not necessary to completely withdraw a trocar tip or the surgical instruments every time the instrument reaches a surgical site or must be advanced further within the patient's body.

Thus, the methods of transluminal surgery of the present invention are substantial improvements over the methods of the prior art. The present invention simplifies transluminal surgery and thus improves the safety and effectiveness of transluminal surgical procedures. The risk of infection, the recovery time, and the pain associated with surgery are all reduced.

Although the invention has been described with reference to a particular arrangement of parts, features, steps, and the like, these are not intended to exhaust all possible arrangements of features or steps, and indeed many other modifications and variations will be ascertainable to those of skill in the art.

What is claimed is:

1. A method of transluminal surgery, comprising the steps of:
   providing an endoscopic surgery apparatus including a tubular member having a plurality of channels along its longitudinal axis, a handle located on a proximal end of the tubular member, two or more arms pivotably connected to a distal end of the tubular member, wherein two or more of said arms have a guiding channel passing therethrough adapted to receive an endoscopic surgical tool passed from one of the plurality of channels through the guiding channel and wherein each of the two or more arms having a guiding channel are pivotably connected to the distal end of the tubular member by a single hinge;
   inserting the distal end of the tubular member through a natural body orifice into a body cavity with the arms in a closed position;
   creating an incision in a body cavity wall sized to accommodate the tubular member using at least one endoscopic surgical tool;
   advancing the distal end of the tubular member through the incision to a desired surgical site;
   pivoting the arms about the hinges into an open position using a mechanism on the handle such that the guiding channels passing through the arms create a desired degree of triangulation for endoscopic surgical tools disposed in the guiding channels;
   performing at least one surgical task at the surgical site; and
   pivoting the arms about the hinges into a closed position using a mechanism on the handle.

2. The method of claim 1, wherein the step of creating an incision in a body cavity wall further comprises the steps of pivoting the arms about the hinges into an open position using a mechanism on the handle such that the guiding channels passing through the arms create a desired degree of triangulation for endoscopic surgical tools disposed in the guiding channels;
   using at least one endoscopic surgical tool to create the incision; and
   pivoting the arms about the hinges into a closed position using a mechanism on the handle.

3. The method of claim 1, wherein the step of creating an incision in a body cavity wall further comprises the steps of advancing an endoscopic surgical tool from the tubular member through an opening between the arms, wherein the arms include a ramp for deflecting the endoscopic surgical tool;
   using the endoscopic surgical tool to create the incision; and
   withdrawing the endoscopic surgical tool into the tubular member.

4. The method of claim 1, wherein the step of advancing the distal end of the tubular member to a desired surgical site further comprises the step of pivoting the arms about the hinges into an open position using a mechanism on the handle so as to provide a wider view of an area proximal to the distal end via an optical channel disposed in the tubular member.

5. The method of claim 1, wherein the step of advancing the distal end of the tubular member to a desired surgical site further comprises the steps of:
insufflating the abdominal cavity using an insufflation channel disposed in the tubular member; and
monitoring the pressure in the abdominal cavity in the region adjacent to the distal end of the tubular member via an insufflation channel disposed in the tubular member.

6. The method of claim 1, wherein the step of performing at least one surgical task at the surgical site further comprises the step of introducing a device for delivery of fluid or gaseous matter through a channel in the tubular member for the delivery of fluid or gaseous matter to the surgical site.

7. The method of claim 1, wherein the step of performing at least one surgical task at the surgical site comprises the step of providing an endoscopic retrieving bag for the removal of dissected tissue.

8. The method of claim 1, further comprising the step of closing the incision in the body cavity wall using at least one endoscopic surgical tool to attach a surgical clip to the incision.

9. The method of claim 1, further comprising the step of closing the incision in the body cavity wall using at least one endoscopic surgical tool to suture the incision.

10. The method of claim 9, wherein the step of closing the incision is performed by a suturing system incorporated into the arms.

11. The method of claim 1, further comprising the step of closing the incision in the body cavity wall using at least one endoscopic surgical tool to employ an endoloop to the incision.

12. The method of claim 1, wherein the step of performing at least one surgical task at the surgical site comprises the step of employing a cauterizing endoscopic surgical tool.

13. The method of claim 1, wherein the step of performing at least one surgical task at the surgical site comprises the step of employing a laser.

14. The method of claim 1, wherein the step of providing an endoscopic surgery apparatus further comprises that the distal end of the tubular member articulates.

15. The method of claim 1, wherein the step of advancing the distal end of the tubular member to a desired surgical site further comprises the step of articulating the distal end of the tubular member into a desired position relative to a surgical site.

16. The method of claim 1, wherein the steps of pivoting the arms about the hinges into an open position a first and a second time further comprise the step of displacing tissue using the arms.

17. The method of claim 1, wherein the step of providing an endoscopic surgery apparatus further comprises that the arms are interchangeable with arms of different configurations; and
the method further comprises the step of selecting two arms having a desired configuration from a group of interchangeable arms of different configurations.

18. The method of claim 17, wherein the step of selecting two arms having a desired configuration includes selecting arms adapted to grasp tissue.

19. The method of claim 17, wherein the step of selecting two arms having a desired configuration includes selecting arms adapted to cut tissue.

20. The method of claim 17, wherein the step of selecting two arms having a desired configuration includes selecting arms which form an obturator shape when the arms are in a closed position.

21. The method of claim 1, wherein the step of providing an endoscopic surgery apparatus further comprises that one of said channels is an optical channel for the transmission of images and at least one other of said channels is an illumination channel for the transmission of light and wherein when the arms are in a closed position an opening is defined for viewing of an area proximal to the distal end via said optical channel and illumination of an area proximal to the distal end via said at least one illumination channel; and
wherein the step of advancing the distal end of the tubular member to a desired surgical site further comprises the step of using the optical channel to view an area proximal to the distal end of the tubular member.

22. The method of claim 1, further comprising the step of using the arms to hold tissue resected from a patient's body for removal from the patient's body.

\* \* \* \* \*